United States Patent [19]

Kobayashi et al.

[11] Patent Number: 5,367,554
[45] Date of Patent: Nov. 22, 1994

[54] X-RAY DIAGNOSTIC APPARATUS OF A CIRCULATORY ORGAN SYSTEM

[75] Inventors: Tohru Kobayashi, Kuroiso; Shuzo Yamamoto, Tochigi; Hiroshi Sakaniwa, Otawara; Satoshi Ohta, Imaichi, all of Japan

[73] Assignee: Kabushiki Kaisha Toshiba, Kawasaki, Japan

[21] Appl. No.: 936,632

[22] Filed: Aug. 28, 1992

[30] Foreign Application Priority Data

Aug. 29, 1991 [JP] Japan ................................ 3-218473

[51] Int. Cl.$^5$ ................................ H05G 1/02
[52] U.S. Cl. ................................ 378/196; 378/197
[58] Field of Search ................ 378/195, 196, 197

[56] References Cited

U.S. PATENT DOCUMENTS 4,922,512  5/1990  Lajus ................................ 378/197
5,095,501  3/1992  Kobayashi ........................ 378/196

Primary Examiner—Craig E. Church
Attorney, Agent, or Firm—Oblon, Spivak, McClelland, Maier & Neustadt

[57] ABSTRACT

An X-ray diagnostic apparatus comprising X-ray generating unit for generating an X-ray to a patient, X-ray image detecting unit, provided to be apposite to the X-ray generating unit to sandwich the patient therebetween, for detecting an X-ray image, a holding apparatus for rotatably holding the X-ray generating unit and x-ray image detecting unit at a rotation axis, which is a line connecting the X-ray generating unit to the X-ray image detecting unit, and a supporting apparatus for rotatably supporting the holding apparatus at the same rotation axis.

5 Claims, 15 Drawing Sheets

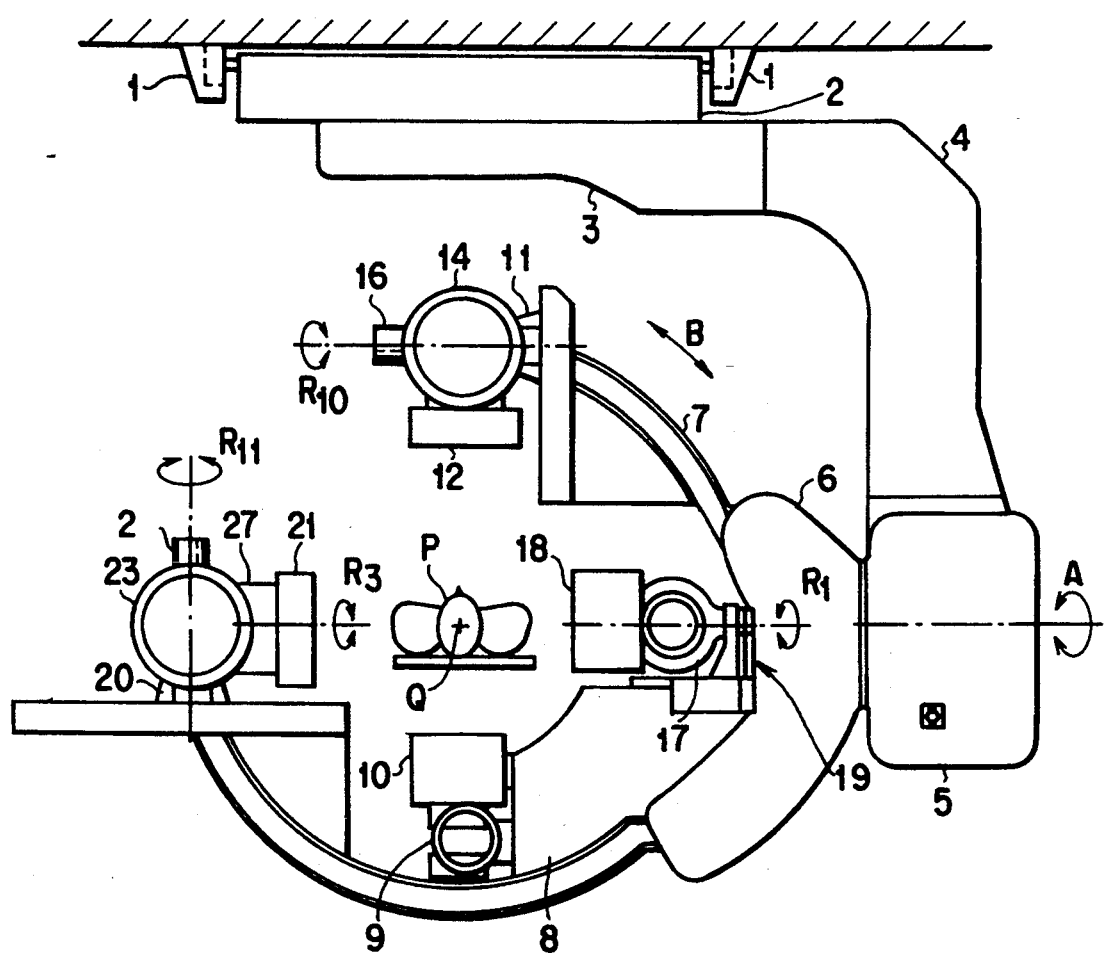
F I G. 2

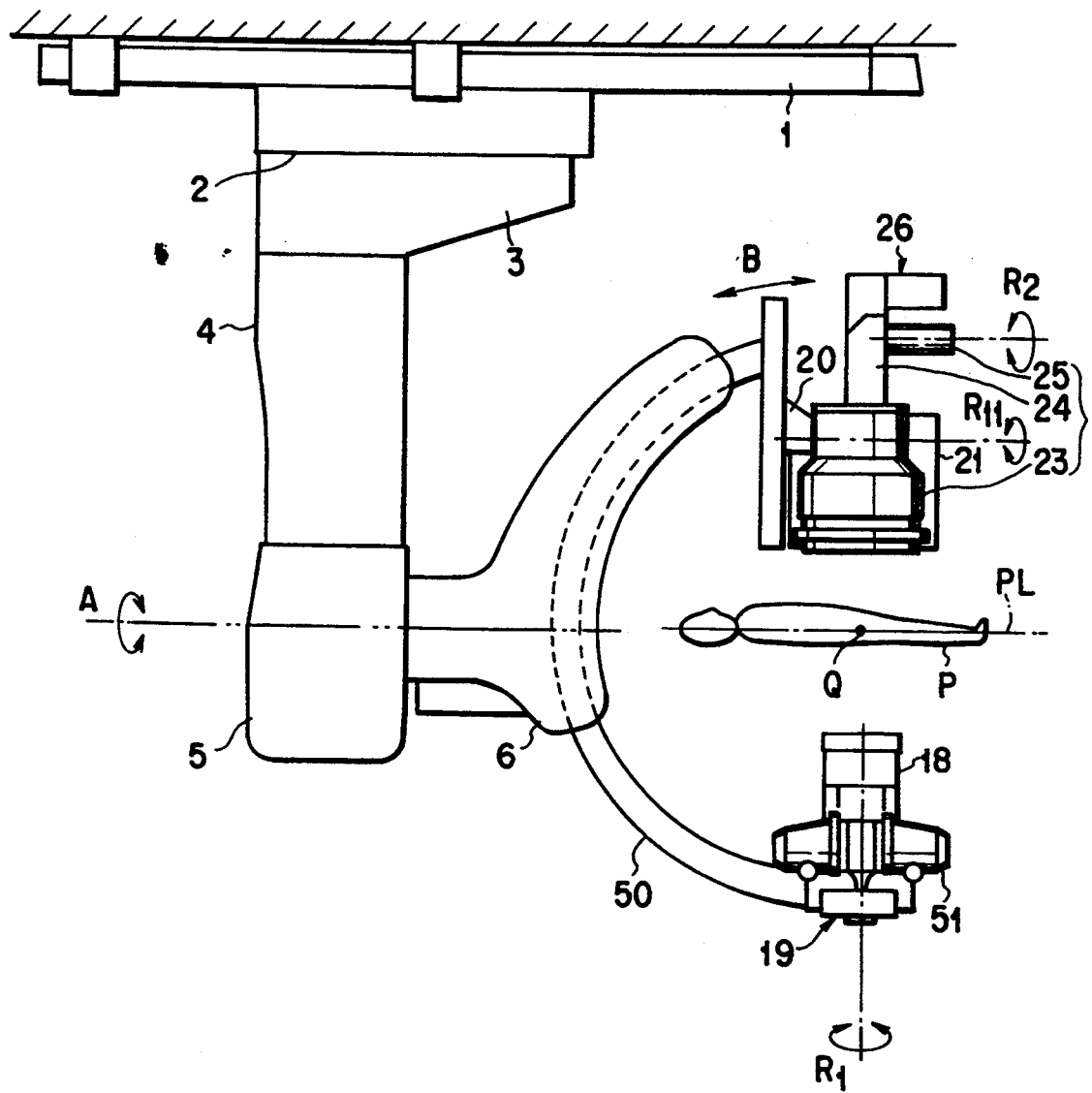
F I G. 10

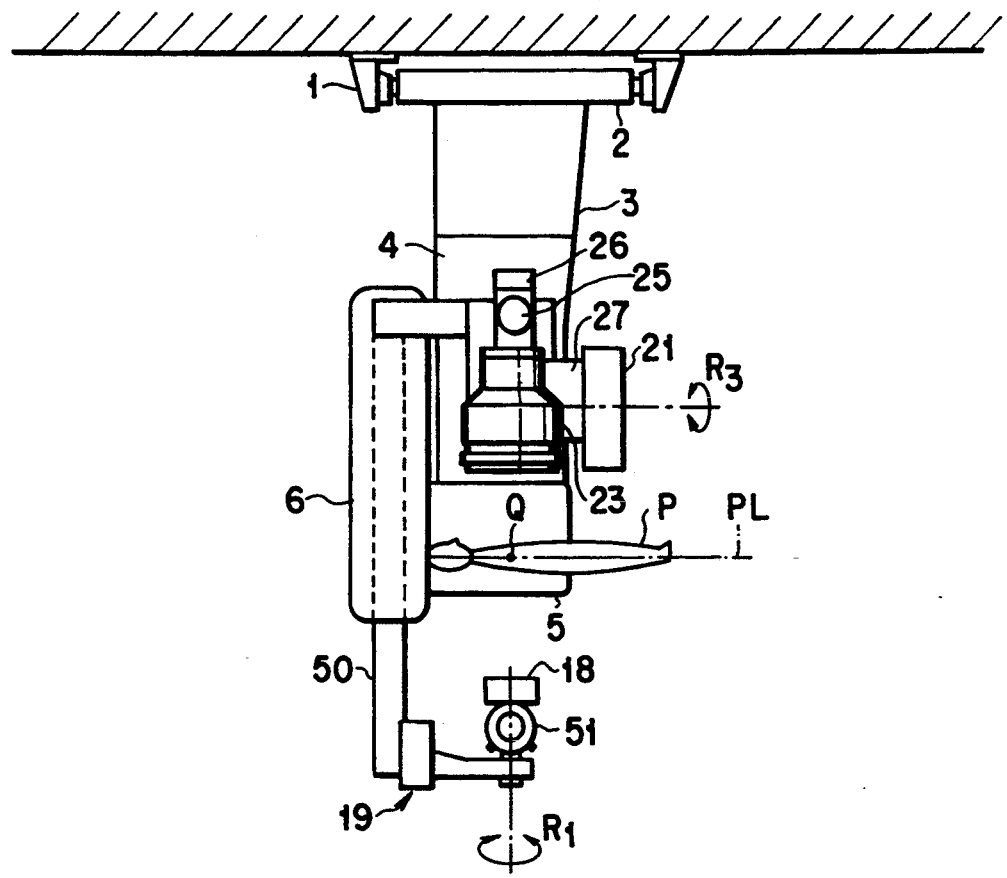
F I G. 11
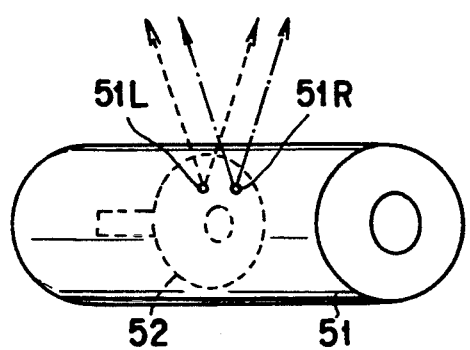
F I G. 12

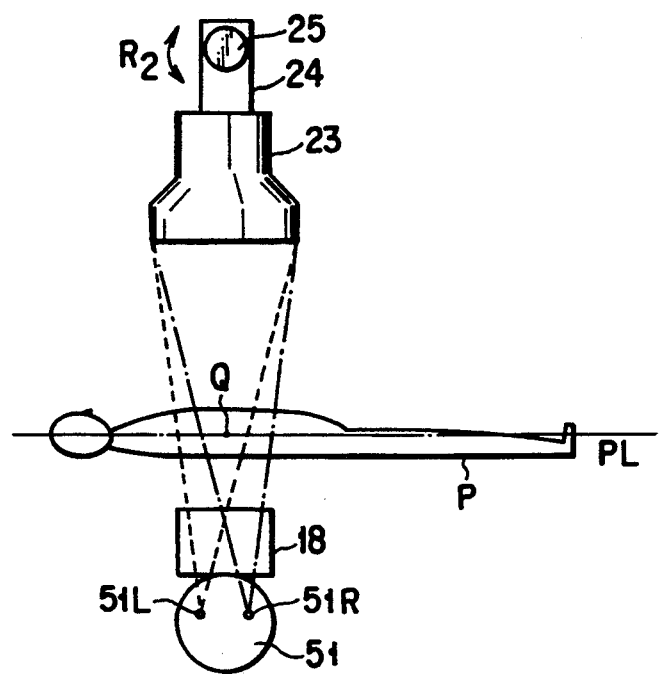
F I G. 13
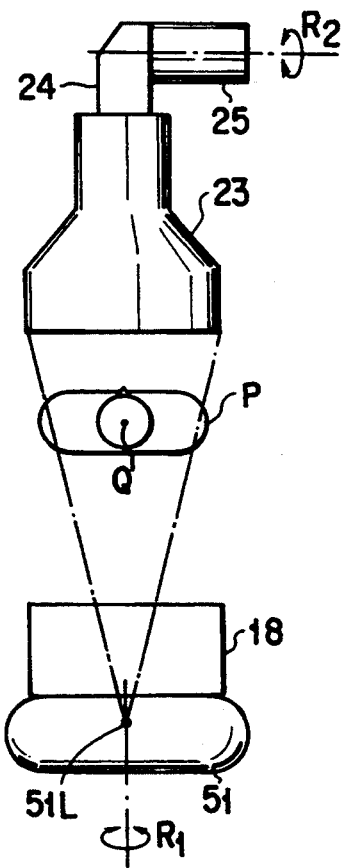
F I G. 14

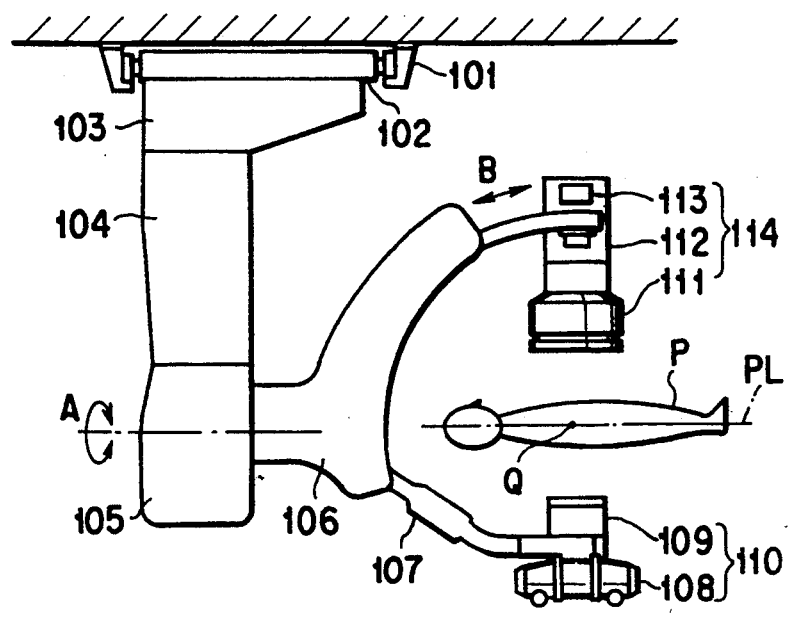
F I G. 23
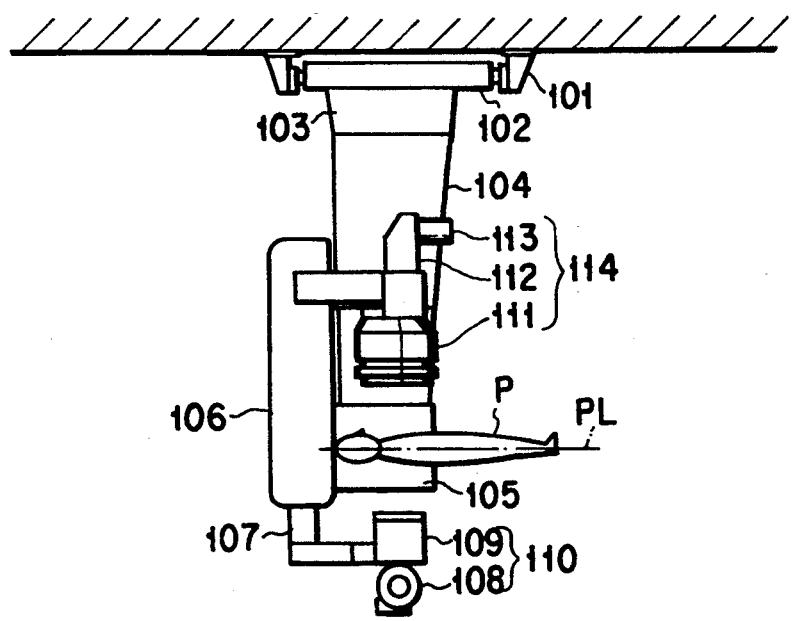
F I G. 24

1

X-RAY DIAGNOSTIC APPARATUS OF A CIRCULATORY ORGAN SYSTEM

BACKGROUND OF THE INVENTION

1. Field of the Invention

The present invention relates to an X-ray diagnostic apparatus of a circulatory organ system to be used to inspect the circulatory organ system.

2. Description of the Related Art

An X-ray diagnostic apparatus of a circulatory organ system is an apparatus for X-ray inspecting a heat, a coronary artery, an abdominal blood vessel, or a blood vessel of lower limbs so as to catch the circulation of blood, running of blood vessel, form of blood vessel, and movement of the valves by injecting a radiopaque substance into the blood vessel and following the flow of image-forming agent. As compared with the other X-ray diagnostic apparatus of a digestive organ system, the technique of much shorter time X-ray irradiation and much higher speed image-forming are required since the object, which the diagnostic apparatus of a circulatory organ system inspects, is the circulation of blood, which moves, the fastest in the human body.

Moreover, the blood vessel, particularly, the blood vessel of the heart or the blood vessel of the encephalon, complicatedly runs around the heart or the encephalon, making, it difficult to observe the running state by an image, which is imaged-formed in one direction. Therefore, it is required that the image-forming be made in the multi-direction. There has been developed the so-called simultaneous, two directional image-forming apparatus wherein a supporting mechanism of image-forming system, having a good operating ability, such that the multi-directional image-forming can be performed, and a simultaneous image-forming is performed in the two directions. Moreover, the technique of the stereoscopic vision, which can observe the complicated running state of the blood vessel as it is, has been developed and practically used.

FIG. 19 is a view explaining the principle of the stereoscopic vision (stereophotographing).

An X-ray tube 90 has a focal point 91R for a right eye and a focal point 91L for a left eye, which are arranged to be spaced from each other in accordance with a distance (parallax) between right and left eyes of the human being. An observer can obtain perspective when he observes two films 92 image-formed at two focal points 91R and 91L with his right and left eyes.

FIG. 20 is a side view of a conventional ceiling suspension type simultaneous two directional image-forming apparatus. This simultaneous two directional image-forming apparatus has its image-forming system supported by a ceiling base 102 movably supported to two rails 101 provided on the lower surface of the ceiling in its back and front direction, an arm base 103 rotatably supported by the ceiling base 102, a suspension arm 104 expandable in a direction that the arm is supported, a support block 105 attached to the suspension arm 104, a ring base 106 rotatably supported by the support block 105 in a direction of an arrow A, and a C-shaped ring 107 supported by the ring base 106 to be slidable in a direction of an arrow B.

In the C-shaped ring 107, two image-forming systems are arranged to be orthogonal to each other at a central point Q of the C-shaped ring 107. The image system, which is arranged to be opposed to a ceiling plate, is hereinafter called "front system" and other image-forming system is hereinafter called "side system."

Both image-forming systems have the same structural elements. That is, both image-forming systems comprise X-ray apparatuses 110 and 111 having an X-ray tube for radiating an X ray and an aperture-setting apparatus for restricting an X-ray radiation field, image systems 112 and 113 having an image intensifier (I.I), which is arranged to be opposed to the X-ray apparatus 110, 111 to sandwich the central point Q therebetween, an optical system, and a TV camera, and a film changer (not shown) for holding an X-ray film.

First, an operator operates the image systems 112 and 113 and changes the operation to the operation of the film changer at a predetermined time as seeing through a patient. Thereafter, the operator image-forms a predetermined image in the film.

The above-structured simultaneous two-directional image-forming apparatus can simultaneously image-form the patient P in two direction orthogonal to each other in the form of dorsal decubits without moving the patient P.

However, as shown in FIG. 21, the ring base 106 is rotated in the direction of arrow A to the support block 105 in order to carry out the so-called inclination image-forming, that is, the image-forming is carried out at an inclination of an angle other than 90° to an body axis PL of the patient by use of the front system. As a result, the side system is rotated in accordance with the rotation of the ring base 106, and the image displayed on a monitor is rotated, and such an image is difficult to observe.

The same point can be said in the case that the film changer is operated at a predetermined time and the X-ray image is formed in the film. That is, the film changer is rotated in accordance with the rotation of the ring base 106, and the X-ray image is formed in the film in the inclination form.

The image-forming has been conventionally performed in a state that the patient is standing erect or lying horizontally, and the diagnosis can be easily performed in such a state in view of sensibility. Conventionally, the film was inclined and attached to the sheet film viewer such that the image formed in the film in the inclination form is changed to the above erect state, and this was extremely inconvenient.

In order to solve the above problem, as shown in FIG. 22, there was developed an apparatus in which only the side system is held on the C-shaped ring 107, and an auxiliary arm 120 for holding the front system is provided separately from the C-shaped ring 107, and so that the front system and the side system can be separately rotated. According to this apparatus, only the auxiliary arm 120 may be rotated when the inclination image-forming is performed, and the original horizontal state of the side system can be maintained.

However, by the provision of the auxiliary arm 120, the structure of the apparatus extremely became complicated, and the apparatus had to be large-sized.

The problems of the stereophotographing will be explained.

FIG. 23 is a side view of a conventional multi-directional image-forming apparatus wherein one image-forming system is provided and the stereophotographing can be performed. FIG. 24 is a front view of FIG. 23, and FIG. 25 is a perspective view showing a focal point of an X-ray tube. The same portions reference numerals are added to the same portions as the portions of FIG. 20, and the explanation is omitted.

As shown in FIG. 25, an X-ray tube 108 has two focal points 108L for a left eye and 108R for a right eye, which are spaced from each other based on the parallax between right and left eyes of the human being, in the surface of a rotation anode 115. The observer can obtain a stereoscopic feeling by seeing two images, which are formed at two focal points 108L and 108R, with his right and left eyes.

However, in a case where the observer wishes to obtain the stereoscopic vision of the erect state, the insertion direction of the patient to the image-forming region is restricted. The reason will be explained as follows:

The case in which the head of the patient P is inserted from the front of the apparatus of FIG. 23 is hereinafter called "front insertion" and the case in which the head of the patient P is inserted from the side of the apparatus of FIG. 24 is hereinafter called "side insertion."

In the case of "front insertion", the X-ray tube 108 and the TV camera 25 are set so as to obtain the erect state of the image of the patient. For example, as shown in FIG. 26, the X-ray tube 108 is mounted on the C-shaped ring 107 such that the focal point 108L is positioned at the right side of the patient P to which the front insertion is provided and the focal point 108R is positioned at the left side thereof. Due to this, in the case of "side insertion", as shown in FIG. 27, two focal points 108L and 108R for the left and right eyes of the X-ray tube are arranged along the body axis PL of the patient P. In a case where the observer performs the stereoscopic vision by the two images obtained in the above state of the arrangement, the stereoscopic vision in which the patient P is lying. For the stereoscopic vision, it is needed that two images are arranged in accordance with the positional relation between two images at the time of image-forming and observed. Due to this, for example, even if the observer views two images for right and left eyes in a state that these two images are rotated at 90°, the observer cannot obtain the desirable stereoscopic vision between the images. As mentioned above, in obtaining the stereoscopic vision of the image of the upright patient, the insertion direction of the patient P to the image-forming region was readily determined by the attaching state of the x-ray tube 108 to the C-shaped ring 107, which was extremely inconvenient.

SUMMARY OF THE INVENTION

An object of the present invention is to provide an X-ray diagnostic apparatus of a circulatory organ system wherein an extremely simple structure is provided, even when a front system is rotated, a side system is not influenced by the rotation and an upright image can be outputted, and an insertion direction of a patient to an image-forming region is not restricted at the time of stereophotographing.

In order to solve the above problems and attain the above object, the present invention provides the following means.

That is, an X-ray diagnostic apparatus of the present invention comprises an X-ray generating unit for generating an X-ray to a patient, X-ray image detecting unit, provided opposite the X-ray generating unit to sandwich the patient therebetween, for detecting an X-ray image. A holding apparatus is provided for rotatably holding the X-ray generating unit and X-ray image deflecting unit about a rotation axis, which is a line connecting the X-ray generating unit to the X-ray image detecting unit. A supporting apparatus is provided for rotatably supporting the holding apparatus about said rotation axis.

According to the X-ray diagnostic apparatus of the present invention, even if the holding apparatus is rotated, X-ray generating means and X-ray image detecting means can be rotated in an inverse direction of the rotation direction of the holding apparatus, thereby making it possible to stop the conventional rotation of an image outputted from X-ray image detecting means in accordance with the rotation of the holding apparatus.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a front view of the first embodiment of the present invention;

FIG. 10 is a side view of a second embodiment of the present invention;

FIG. 11 is a front view of the second embodiment of the present invention;

FIG. 12 is a perspective view showing two focal points of an X-ray tube;

FIG. 13 is a front view showing the relationship between a patient P and two focal points of the X-ray when the side insertion is provided in a first state:

FIG. 14 is a side view showing the relationship between the patient P and two focal points of the X-ray when the side insertion is provided in the first state;

FIG. 23 is a side view of a conventional multi-directional image-forming apparatus;

FIG. 24 is a side view of a conventional multi-directional image-forming apparatus;

DETAILED DESCRIPTION OF THE PREFERRED EMBODIMENTS

A first embodiment of the X-ray diagnostic apparatus of a circulatory organ system relating to the present invention will be explained with reference to the drawings. This embodiment relates to a simultaneous two directional image-forming apparatus having two image-forming systems.

Figure 1:
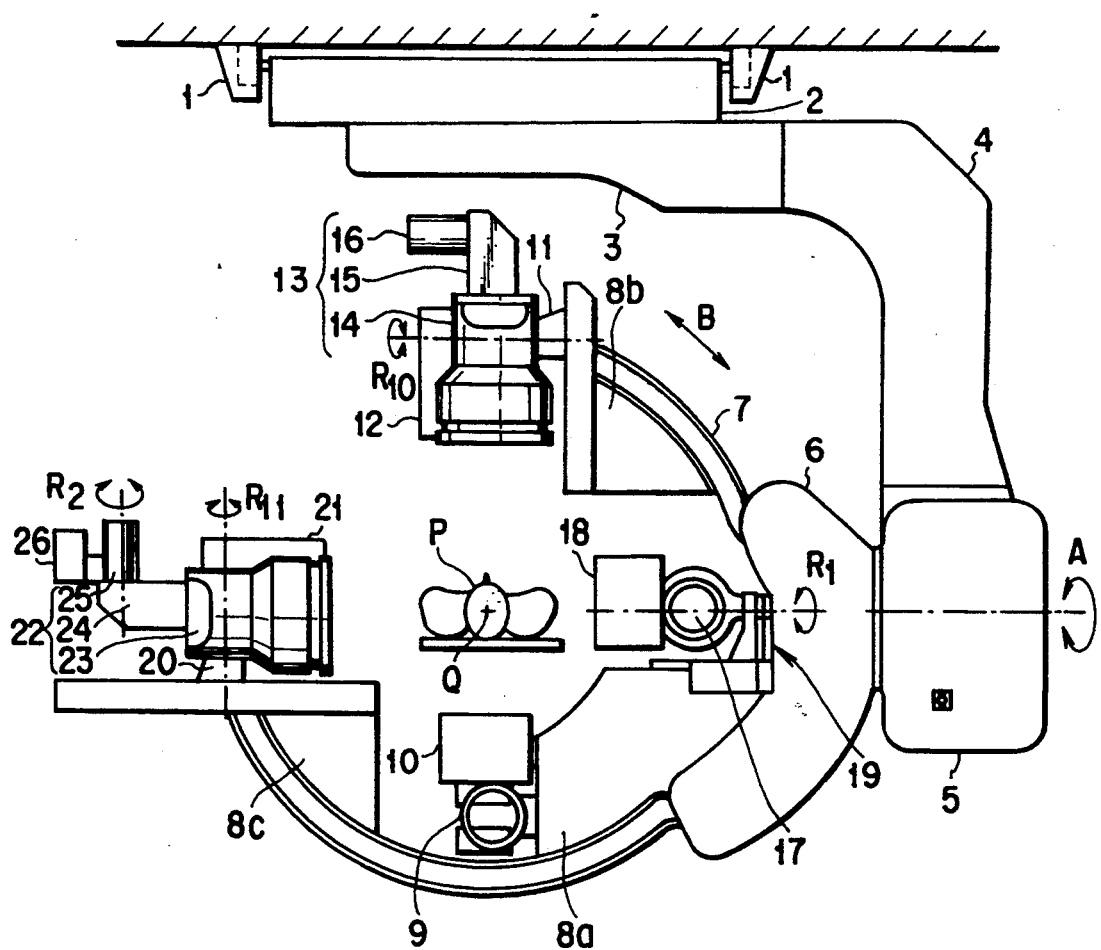
FIG. 1 is a side view of a first embodiment of the present invention.

As shown in FIG. 1, two guide rails 1 are provided to be parallel to a lower surface of a ceiling. A ceiling base 2 is supported to be movable to the guide rails 1 back and forth. A base arm 3 is rotatably supported to the lower surface of the ceiling base 2. An inverse L-shaped suspension arm 4 is attached to the base arm 3. A support block 5 is attached to the lower end of the suspension arm 4, and drives a ring base 6 to be rotated in a direction of an arrow A. A ring base angle detector 44 (not shown) is provided in the support block 5 to detect an inclined angle of the ring base 6 to the perpendicular direction. A C-shaped ring 7 of ¾ circular is supported around a center Q to be slidable on the ring base in a direction of an arrow B. A rotate on central axis (dotted line) of the ring base 6 intersects the center Q of the C-shaped ring 7. Therefore even if the ring base 6 rotates or the C-shaped ring 7 is slid, the position of center Q of the C-shaped ring 7 is not changed.

A block 8a is attached to the inside of the C-shaped ring 7, and an X-ray tube 9 is supported such that the direction of the X-ray radiation is directed to the center Q of the C-shaped ring 7. A collimator 10 for adjusting the range (radiation field) of the X-ray radiated from the X-ray tube 9 is provided on the side of the X-ray radiation of the X-ray tube 9. A block 8b is attached to the inside of the C-shaped ring 7, and supported by the block 8b. A rotation mechanism 11 supports a film changer 12 and an image system 13 to be freely rotatable in a direction of an arrow R10. Therefore, according to the present apparatus, an image intensifier 14 of the image system 13 and the film changer 12 can be selectively opposed to the X-ray tube 9, and the changing of a perspective operation and a film image-forming operation can be set. FIG. 2 shows the state that the film changer 12 is opposed to the X-ray tube 9 by that the image system 13 and the film changer 12 are rotated in the direction of arrow R10. FIG. 2 also shows the state that a film changer 21 is opposed to an X-ray tube 17 by that an image system 22 and the film changer 21 are rotated in the direction of an arrow R11.

As shown in FIG. 1, an optical system 15 including a lens and a prism is provided at the back of the image intensifier 14, and an optical axis from the image intensifier 14 is curved, and an optical image is guided to an image region of a TV camera 16. The optical image to be outputted from the optical system 15 is image-formed by the TV camera 16, and supplied to an image display including a monitor (not shown).

The X-ray image-forming system comprising the X-ray tube 9 including the collimator 10, film changer 12, and image system 13 is hereinafter called "front system."

The present simultaneous two directional image-forming apparatus has an other X-ray image-forming system (hereinafter called "side system") other than the front system. The side system comprises an X-ray tube 17, a collimator 18, a film changer 21, and an image system 22. The image system 22 comprises an image intensifier 23, an optical system 24, and a TV camera 25. The side system is arranged such that the image-forming axis of the side system, which is a line connecting an X-ray tube 17 to a film changer 21 or an image intensifier 23, is orthogonal to that of the front system at the center Q of the C-shaped ring 7.

By an X-ray tube rotation mechanism 19 held by the block 8a, the X-ray tube 17 is supported in the direction of arrow R1 to be freely rotatable at a rotation axis which coincides with the image-forming axis of the side system. Since the collimator 18 is attached to the X-ray tube 17, the aperture-setting controller 18 is rotated in accordance with the rotation of the X-ray tube 17.

Figure 3:
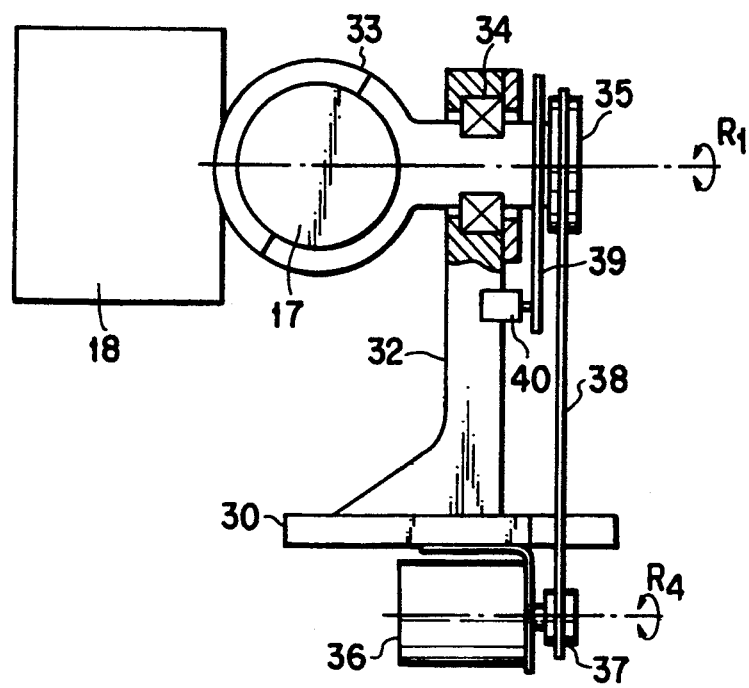
FIG. 3 is a side view of a rotation mechanism of an X-ray apparatus.
Figure 4:
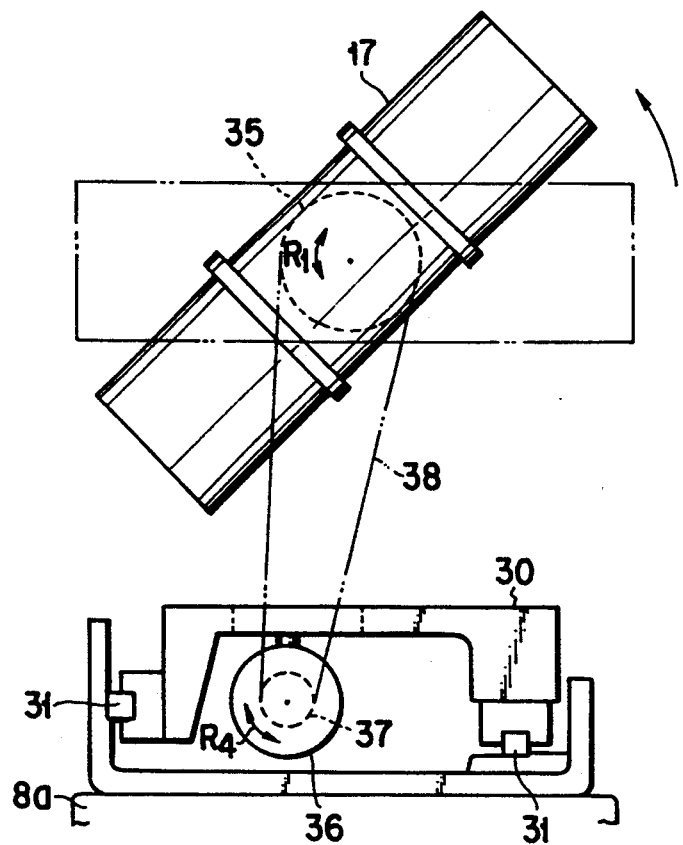
FIG. 4 is a front view of a rotation mechanism of an X-ray apparatus.

FIG. 3 is a side view showing the X-ray tube rotation mechanism 19, and FIG. 4 is a front view of FIG. 3. A base 30 is slidably supported on a linear rail 31, which is provided on the block 8a to be parallel with the image-forming axis of the side system. The base 30 can slide the X-ray tube 17 close to the center Q of the C-shaped ring 7 or away therefrom. A support 32 is provided on the base 30. A supporting fork 33 for supporting the X-ray tube 17 is rotatably supported by the support 32 via a bearing 34. Its rotation axis is set to conform to the image-forming axis of the side system. The X-ray tube 17 can be rotated in the direction of arrow R1 without changing the image-forming axis. A motor 36, having a braking function, is provided in the base 30 to be rotated around the rotation axis parallel to the rotation axis of the supporting fork 33. A sprocket 37 is provided in the rotation axis of the motor 36. A chain 38 is placed between the sprocket 37 and a chain sprocket 35 provided in the supporting fork 33. Then, the rotation of the sprocket 37 is transmitted to the chain sprocket 35. Thus, supporting fork 33, X-ray tube 17, and aperture-setting tube 18 are rotated. A rotation plate 39 is attached to the supporting fork 33, and rotated together with the supporting fork 33. An angle detector 40 is provided in the support 32 in accordance with the rotation passage of the rotation plate 39, and detects the rotation angle of the X-ray tube 17.

A block 8c is attached to the inside of the C-shaped ring 7, and a rotation mechanism 20 is supported by the block 8c. The rotation mechanism 20 rotatably supports the film changer 21 and the image system 22 in the direction of R11. Thus, the image intensifier 23 of the image system 22 and the film changer 21 can be selectively opposed to the X-ray tube 17.

The film changer 21 is rotatably supported in the direction of arrow R3 by a film changer rotation mechanism 27 similar to the X-ray tube mechanism 19 (see FIG. 2).

The TV camera 25 is provided on the optical system 24 to be freely rotatable in the direction of arrow R2 by a camera rotation mechanism 26 in a state that an optical axis from the optical system 24 is used as a rotation axis.

Since the structure of the camera rotation mechanism 26 and that of the film changer rotation mechanism 27 are similar to that of the X-ray tube rotation mechanism 19, the explanation will be omitted. Similarly to the X-ray tube rotation mechanism 19, a camera angle detector 47 is provided in the camera rotation mechanism 26. Thus, the rotation angle to the initial position of the TV camera may be detected. Moreover, a detector angle detector 49 is provided in the film changer rotation mechanism 27, and the rotation angle of the film changer 21 to the vertical position may be detected.

Figure 5:
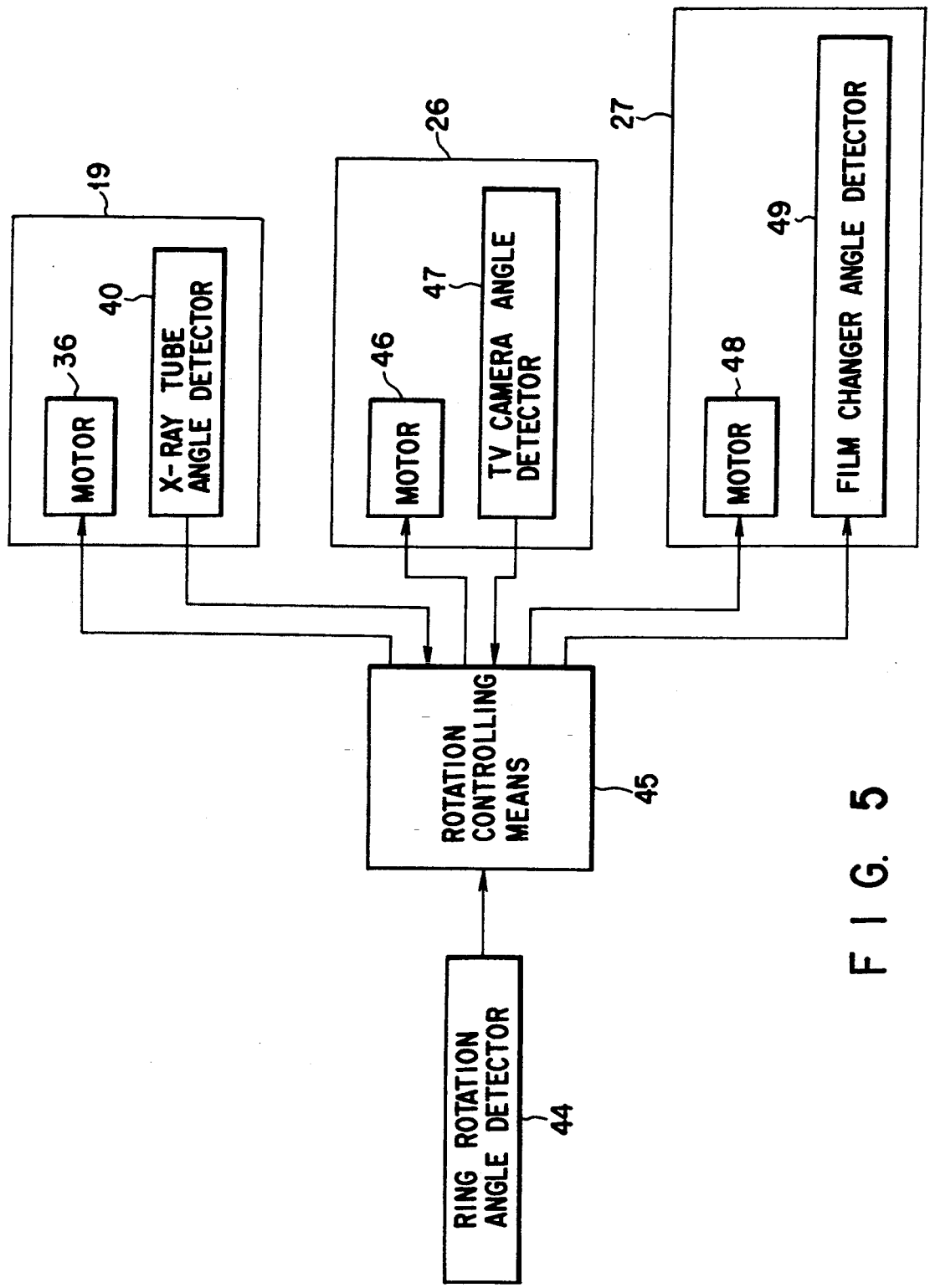
FIG. 5 is a block diagram of rotation controlling means.

As shown in FIG. 5, a rotation controller 45 inputs angle data of the ring base 6 detected by a ring base angle detector 44, and inputs angle data of the X-ray tube 17 detected by an X-ray tube angle detector 40 of the X-ray tube rotation mechanism 19. The rotation controller 45 supplies a drive signal to the motor 36 comparing the angle data. Thereby, the X-ray tube 17 and the collimator 18 are rotated in the direction opposite to the rotation direction of the ring base 6 by the rotation angle of the ring base 6, and the horizontal position is maintained.

Moreover, rotation controller 45 inputs angle data of the ring base 6 detected by a ring base angle detector 44, and inputs angle data of the TV camera 25 detected by a TV camera angle detector 47 of the camera rotation mechanism 26. The rotation controller 45 supplies a drive signal to a motor 46 thus driving the TV camera 26 as comparing this angle data. Thereby, the TV camera 25 is rotated in the direction conforming to the direction of the ring base 6 by the rotation angle of the ring base 6, and can follow the rotation of the optical image from the optical system 24.

Furthermore, rotation controller 45 inputs angle data of the ring base 6 detected by a ring base angle detector 44, and inputs angle data of the film changer 21 detected by a film changer angle detector 49 of the film changer rotation mechanism 27. The rotation controller 45 supplies a drive signal to a motor 48 driving the film changer 21 comparing this angle data. Thereby, the film changer 21 is rotated in the direction opposite to the rotation direction of the ring base 6 by the rotation angle of the ring base 6, and the horizontal position can be maintained.

The following will explain the operation of the above-structured simultaneous two-directional diagnostic apparatus according to the embodiment of the present invention.

Figure 6:
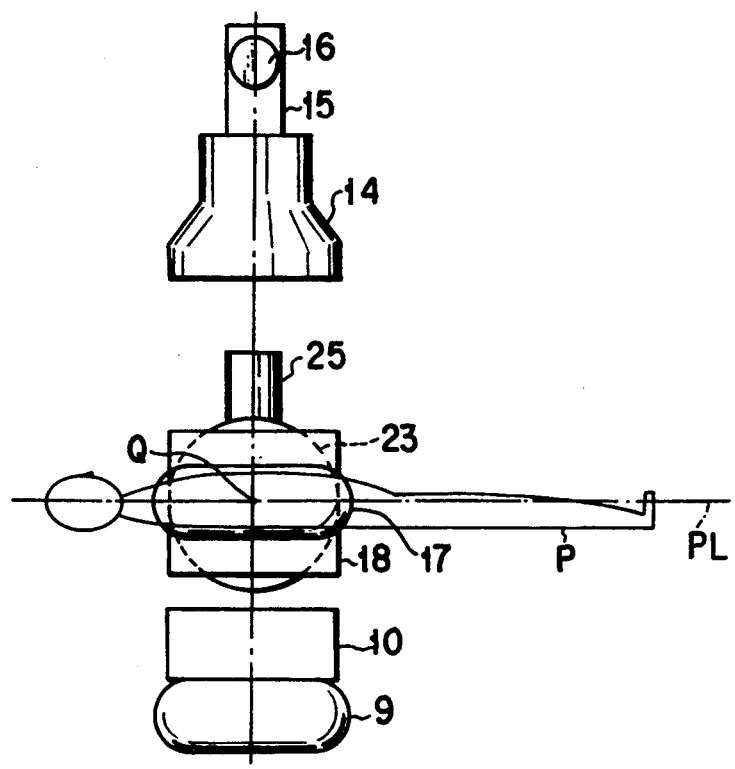
FIG. 6 is a front view showing a side system and a front system when a ring base is in a vertical direction, that is, an initial state.
Figure 7:
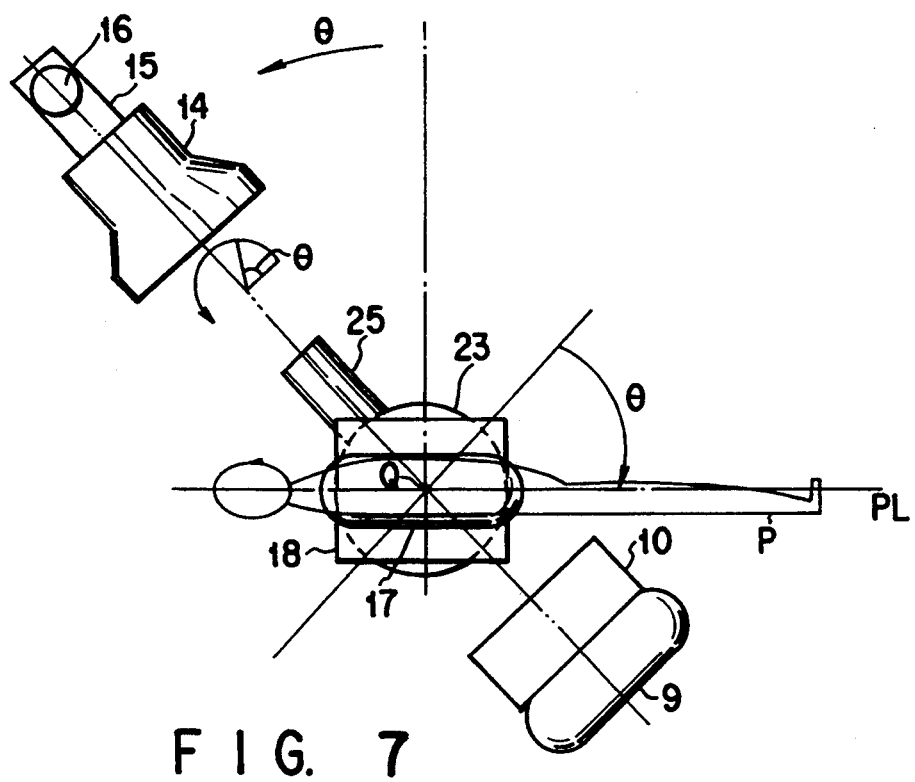
FIG. 7 is a front view showing the side system and the front system when the ring base is in an inclination state, that is, the ring base is rotated.

FIG. 6 is a view showing the side system and the front system when the ring base 6 is in a vertical direction, that is, an initial state. FIG. 7 is a view showing the side system and the front system when the ring base 6 is in an inclination state, that is, the ring base 6 is rotated. Since the state of the rotation of the film changer 21 is the same as that of the X-ray tube 17, the explanation is omitted.

It is assumed that the ring base 6 is rotated to a head portion of a patient P, and changed from the initial state of FIG. 6 to the inclination state of FIG. 7. At this time, the rotation angle of the ring base 6 is $\theta$. The rotation angle $\theta$ is detected by the ring base angle detector 44, and supplied to the rotation controller 45. Moreover, angle data of the X-ray tube 17 to be detected by the X-ray tube angle detector 40 and angle data of the TV camera 25 to be detected by a TV camera angle detector 47 of the camera rotation mechanism 26 are supplied to rotation controller 45.

Rotation controller 45 inputs angle data of the ring base 6 detected by the ring base angle detector 44, and angle data of the X-ray tube 17 to be detected by the X-ray tube angle detector 40 of the X-ray tube rotation mechanism 19. Rotation controller 45 supplies the drive signal to the motor 36 by comparing this angle data. Thereby, the X-ray tube 17 and the collimator 18 are rotated in the direction opposite to the rotation direction of the ring base 6 by the rotation angle of the ring base 6, and the horizontal position is maintained.

Moreover, rotation controller 45 inputs angle data of the ring base 6 detected by the ring base angle detector 44, and angle data of the TV camera 25 detected by the TV camera angle detector 47 of the camera rotation mechanism 26. The rotation controller 45 supplies the drive signal to the motor 46 driving the TV camera 26 to be rotated as comparing this angle data. Thereby, the TV camera 25 is rotated in the direction conforming to the direction of the ring base 6 by the rotation angle of the ring base 6, and can follow the rotation of the optical image from the optical system 24.

Figure 19:
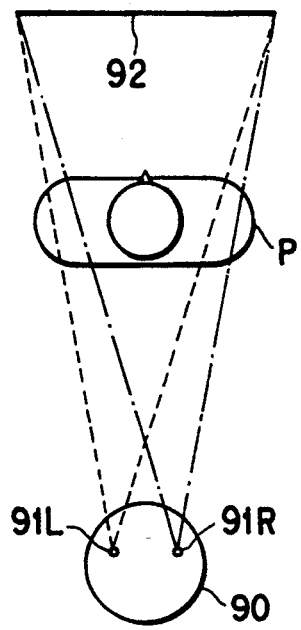
FIG. 19 is a view explaining the principle of the stereophotographing.
Figure 20:
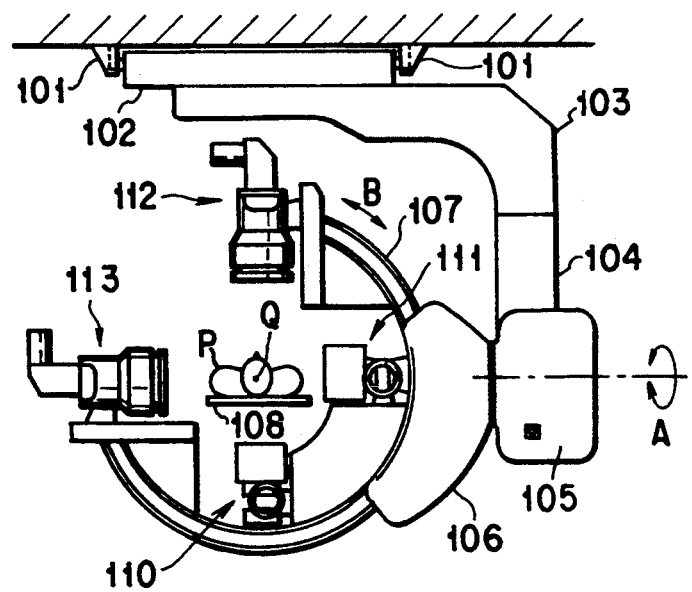
FIG. 20 is a side view of a conventional simultaneous two-directional image-forming apparatus.
Figure 21:
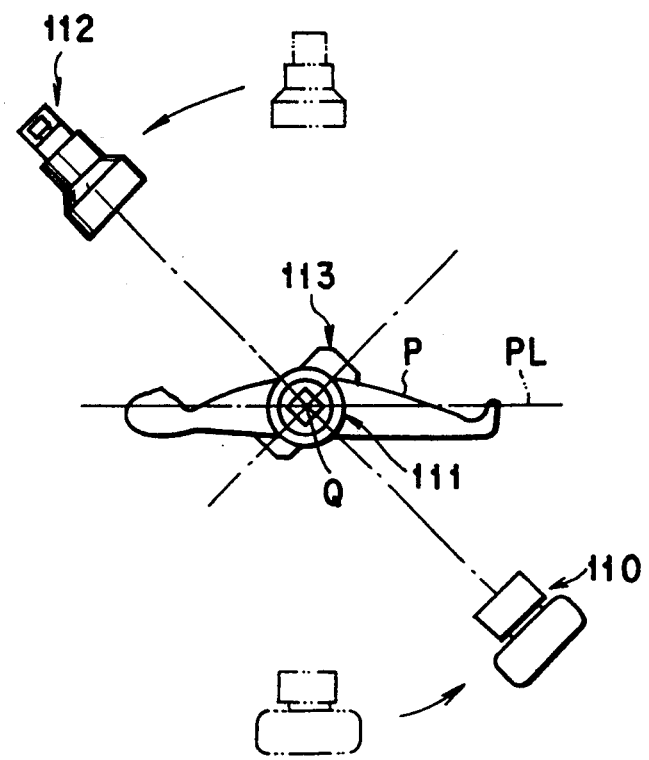
FIG. 21 a view explaining the problem of the conventional simultaneous two-directional image-forming apparatus.
Figure 22:
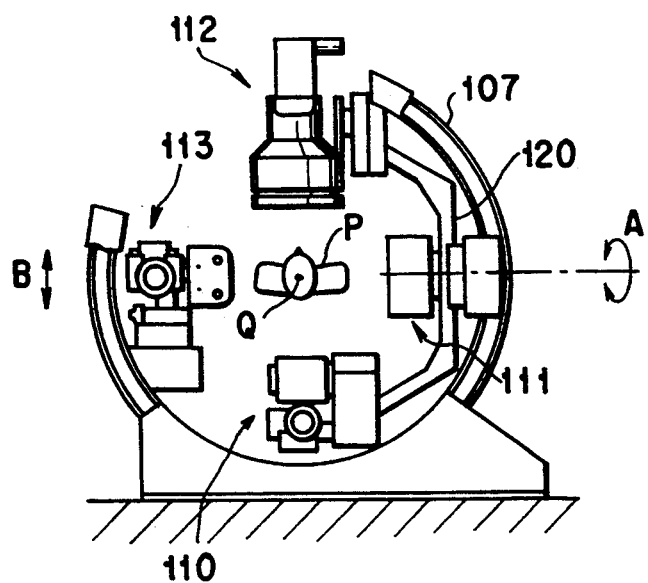
FIG. 22 is a side view of the other conventional simultaneous two-directional image-forming apparatus.
Figure 25:
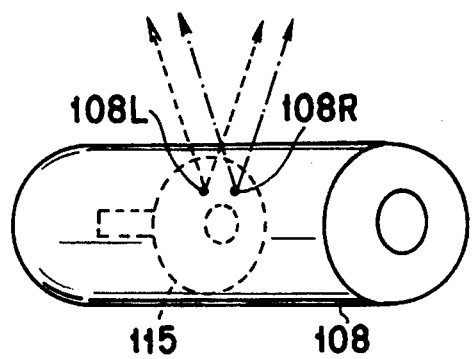
FIG. 25 is a perspective view showing two focal points of the X-ray tube.
Figures 26, 27:
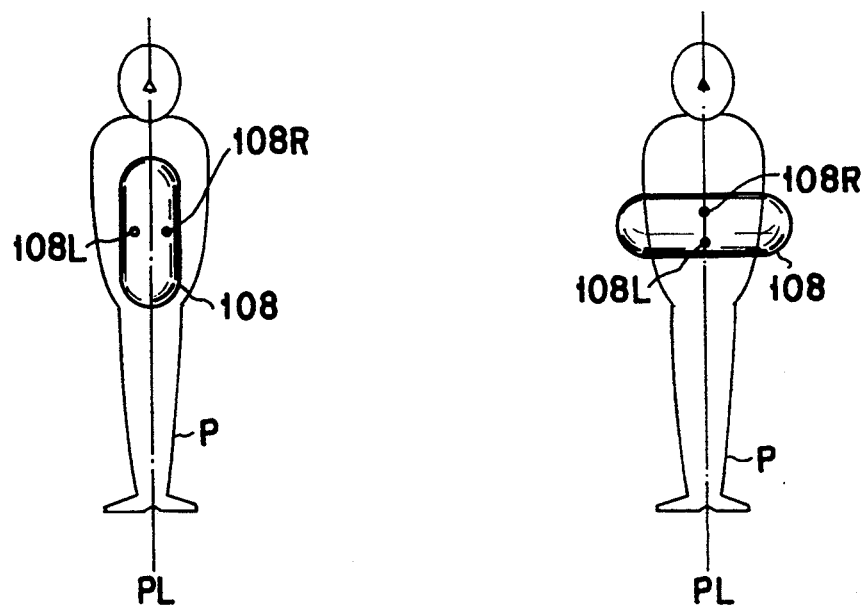
FIG. 26 is a view showing the relationship between the patient P and two focal points of the X-ray when the front insertion is provided by the conventional multi-directional image-forming apparatus.
FIG. 27 is the view showing the relationship between the patient P and two focal points of the X-ray when the side insertion is provided by the conventional multi-directional image-forming apparatus.

Therefore, even if the ring base 6 is rotated, an erect image is outputted from the TV camera 25 of the side system. As a result, the still image is displayed on the monitor even if the ring base 6 is rotated, thereby solving the complication in which the display image is rotated in accordance with the rotation of the ring base 6. Further, according to the above embodiment, the structure can be simplified and miniaturized by the provision of the conventional auxiliary arm shown in FIG. 19.

Figure 8:
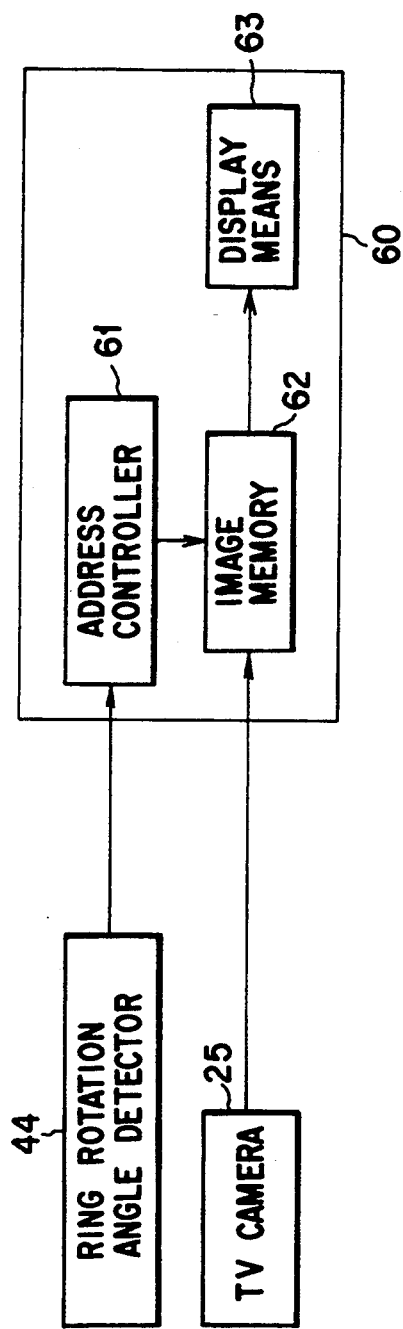
FIG. 8 is a block diagram of an image display device.
Figure 9:
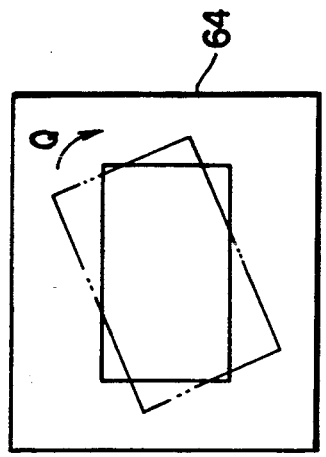
FIG. 9 is a schematic diagram to explain the image rotation.

According to the above embodiment, the rotation of the output image from the side system, which is caused in accordance with the rotation of the ring base, is solved by mechanical means such as the X-ray tube rotation mechanism and the TV camera rotation mechanism. However, as shown in FIG. 8, the rotation of the output image may be canceled by an image display device 60, and the output image may be displayed. An address controller 61 of the image display device 60 inputs inclination angle data detected by the ring base angle detector 44, changes an address signal showing a storing position of an image signal sent from the TV camera 25, and supplies the changed address signal to an image memory 62 storing the image signal to be synchronous with the input of the image signal. FIG. 9 is a view schematically showing a memory region 64 of the image memory 62. In this view, a dotted line shows an image on the memory region 64 when the image outputted from the side system in the inclination manner is stored therein in accordance with the normal address signal. Moreover, a solid line shows an image on the memory region 64 when the image outputted from the side system in the inclination manner is stored therein in accordance with the address signal changed by the address controller 61. The memory region 64 corresponds to the display range of the monitor included in display means 63. The image memory 62 receives the address signal and stores the output image sent from the side system in a state that the output image is inclined by the inclination angle $\theta$ of the ring base 6 so as to cancel the rotation of the image, and outputs the image to display means 63 in accordance with a predetermined order. Thereby, the image is displayed on the monitor of display means 63 so as to cancel the rotation of the ring base 6, and this can solve the complication in which the display image is rotated in accordance with the rotation of the ring base 6.

A second embodiment of the present invention will be explained. FIG. 10 is a side view of this embodiment, FIG. 11 is a front view of this embodiment, and FIG. 12 is a perspective view showing a focal point of the X-ray tube. A method for inserting a patient P shown in FIG. 10 is called "front insertion" and a method for inserting a patient P shown in FIG. 11 is called "side insertion." In FIGS. 10 and 11, the same reference numerals are added to the same portions as the first embodiment, and the specific explanation is omitted.

As shown in FIGS. 10 and 11, according to this embodiment, there is provided a simultaneous two-directional diagnostic apparatus which has one image-forming system, and which can perform stereophotographing. Similar to the first embodiment, the diagnostic apparatus of this embodiment comprises a guide rail 1, a ceiling base 2, an arm base 3, an inverted L-shaped suspension arm 4, a support block 5, and a ring base 6. A semi-circular C-shaped ring 50 is supported in the ring base 6 around the center Q to be freely slidable in a direction of an arrow B.

Similar to the first embodiment, an X-ray tube 51 is supported freely rotatable in a direction of an arrow R1, with respect to an image-forming axis of the image-forming system, by the X-ray rotation mechanism 19 mounted on one end of the ring base 6. As shown in FIG. 12, the X-ray tube 51 has a focal point 51R for a right eye and a focal point 51L for a left eye, which are set away from the surface of a rotation anode 52 to be able to stereograph a subject. The collimator 18 is provided on the X-ray radiation side of the X-ray tube 51, and rotated together with the rotation of the X-ray tube 51.

Similar to the first embodiment, the film changer 21 and the image system 22 are supported freely rotatable in the direction of the arrow R1 by the rotation mechanism 20, and are selectively opposed each other to sandwich the X-ray tube 51 and the center Q of the ring base 6.

The image system 22 comprises the image intensifier 23, the optical system 24, which is arranged on the output side of the image intensifier 23 and changes the optical axis of the output image, and the TV camera 25, which image-forming the output image sent from the optical system 24. Similar to the first embodiment, the TV camera 25 is supported freely rotatable around the optical axis from the optical system 24 to the optical system 24 in the direction of the arrow R2.

Similar to the first embodiment, the apparatus of the second embodiment has rotation control means for controlling the X-ray tube rotation mechanism 19, the camera rotation mechanism 22, and the film changer rotation mechanism 27. In the rotation controlling means, there are provided a first switch corresponding to the "front insertion" and a second switch corresponding to the "side insertion." Rotation controlling means controls the X-ray tube rotation mechanism 19 and the camera rotation mechanism 22, and also rotates the X-ray tube 51 and the TV camera 25 so as to see through or image-form the erect image of the patient P to which "front insertion" is provided when the first switch is designated. Also, Rotation controlling means controls the X-ray tube rotation mechanism 19 and the camera rotation mechanism 22, and also rotates the X-ray tube 51 and the TV camera 25 so as to see through or image-form the erect image of the patient P to which "side insertion" is provided when the second switch is designated.

The operation of the above-structured apparatus of the second embodiment will be explained.

The first switch is designated, and the X-ray tube 51 and the TV camera 25 are controlled by rotation controlling means so as to be set to in an initial state (first state) that the erect image can be outputted when "front insertion" is provided. Since the rotation of the film changer 21 is the same as that of the X-ray tube 51, the explanation is omitted.

FIG. 13 is a front view showing the relation between the patient P to which "side insertion" is provided and two focal points of the X-ray in the first state. FIG. 14 is a side view of FIG. 13. As shown in FIGS. 13 and 14, the focal points 51R and 51L for right and left eyes of the X-ray tube 51 are arranged to be parallel to the body axis PL of the patient P. In this state, if the right and left images outputted from the image-form system are displayed on the monitor as they are, the body axis PL is horizontally displayed on the monitor, and is not erected. Due to this, it is difficult to perform the diagnosis.

Figure 15:
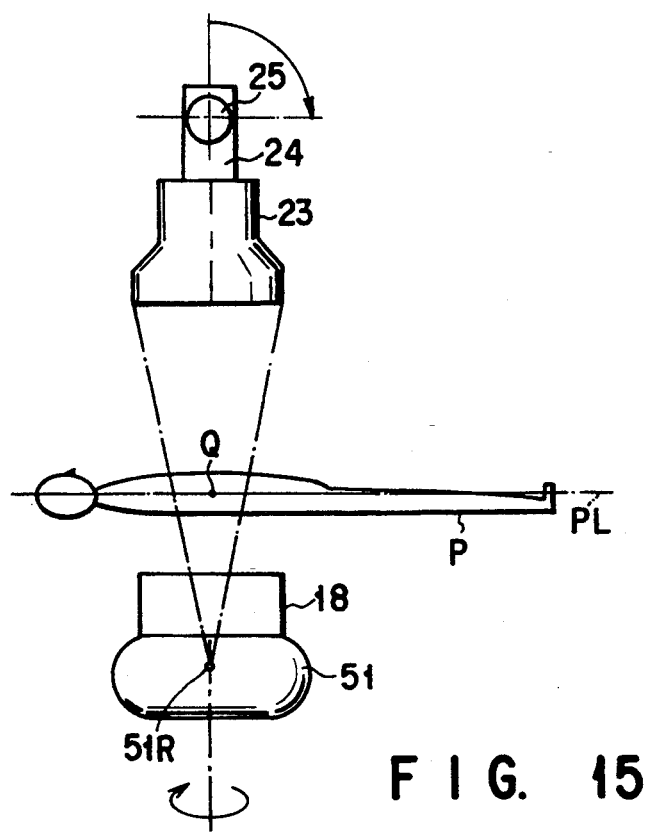
FIG. 15 is a front view showing the relationship between the patient P and two focal points of the X-ray when the side insertion is provided in a second state.
Figure 16:
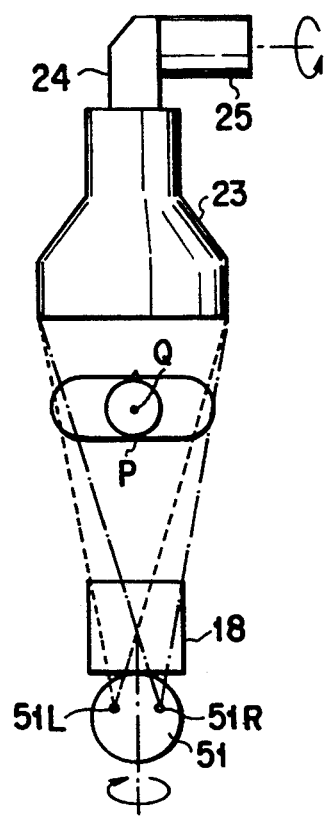
FIG. 16 is a side view showing the relationship between the patient P and two focal points of the X-ray when the side insertion is provided in the second state.

FIG. 15 is a front view showing the relation between the patient P to which "side insertion" is provided and two focal points of the x-ray when the second switch is designated, and FIG. 16 is a side view of FIG. 15. If the second switch is designated in place of the first switch, rotation controlling means drives the X-ray tube rotation mechanism 19 and the TV camera rotation mechanism 26. The X-ray tube 51 and the TV camera 25 are rotated in the direction of the arrow shown in FIGS. 14 and 15, thus the focal points 51R and 51L for right and left eyes of the X-ray tube 51 are positioned on the right and left of the patient P, and the erect image can be outputted.

As mentioned above, according to the above embodiment, the X-ray tube 51 and the TV camera 25 are rotated in the insertion direction of the patient P, and the erect image, which can be easily diagnosed, can be outputted. Thereby, the restriction of the insertion direction to the image-forming region of the patient P can be overcome.

The present invention is not limited to the above-mentioned embodiments. Various modifications can be made without departing from the scope of the invention. In the above embodiment, the X-ray tube rotation mechanism, the camera rotation mechanism, and the film changer rotation mechanism have a motor, and the X-ray tube, TV camera, and film changer are electrically rotated. However, the simple structure in which the X-ray tube, TV camera, and film changer may be manually rotated in place of the electrical motor mechanism motor. Moreover, in the above embodiment. X-ray tube and the collimator mounted on the X-ray tube are rotated. However, only the collimator may be rotated.

Figure 17:
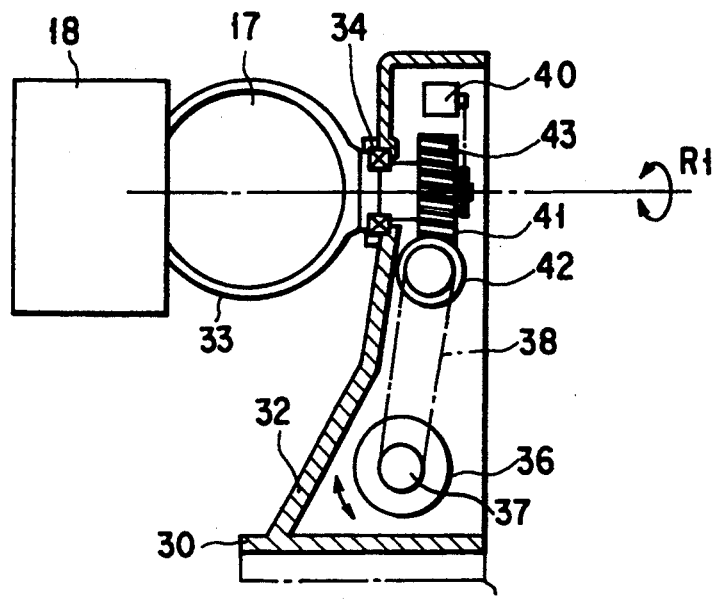
FIG. 17 is a side view of other rotation mechanism of an X-ray apparatus.
Figure 18:
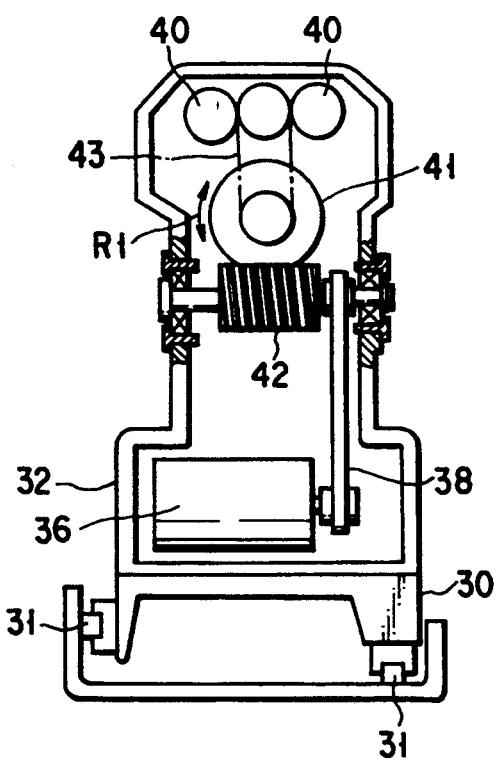
FIG. 18 is a front view of an other rotation mechanism of an X-ray apparatus.

A worm gear set as shown in FIGS. 17 and 18 may be used as X-ray tube rotation mechanism 19. FIG. 17 is a side view of the X-ray tube rotation mechanism 19 corresponding to FIG. 3, and FIG. 17 is a front view of the X-ray tube rotation mechanism 19 corresponding to FIG. 4. The same reference numerals are added to the same portions as FIGS. 3 and 4. A worm wheel 41 and a worm 42, which is driven to be rotated by the motor 36 via the chain 38, constitute a worm gear set. If the worm 42 is rotated, the thread of the worm wheel 41 is thrust, and the worm wheel 41 is rotated in the direction R1. The worm gear set is characterized in that a reduction ratio, which is larger than the general gear set, can be obtained by the small volume. By use of the worm gear set, the X-ray tube rotation mechanism 19 can obtain a sufficient reduction ratio without being large-sized. Moreover, a self lock function is provided in the worm gear set, so that the braking function can be removed from the motor.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An X-ray diagnostic apparatus comprising:
   a C-shaped ring member;
   a first X-ray source unit supported by a first rotation mechanism such that it can rotate about a horizontal axis, said first rotation mechanism being held by said C-shaped ring member along the horizontal axis passing a central point of said C-shaped ring member;
   first X-ray image detecting means supported by a second rotation mechanism such that it can rotate about said horizontal axis, said second rotation mechanism being held by said C-shaped ring member along the horizontal axis at a location opposed to said first X-ray source unit with respect to the central point;
   a second X-ray source unit held by said C-shaped ring member along a vertical axis passing the central point;
   second X-ray image detecting means held by said C-shaped ring member along the vertical axis at a location opposed to said second X-ray source with respect to the central point;
   a base portion holding said C-shaped ring member such that said C-shaped ring member can incline about the horizontal axis; and
   control means for rotating said first X-ray source unit about the horizontal axis together with said first X-ray image detecting means in a direction opposite to a direction of inclination of said C-shaped ring member through an angle identical to the angle of the inclination, thereby controlling said first and second rotation mechanisms so as to keep horizontal said first X-ray source unit and said first X-ray image detecting means.

2. The X-ray diagnostic apparatus according to claim 1, wherein said first X-ray source unit comprises an X-ray source for radiating X-rays and a collimator for collimating the X-rays within a predetermined range; said first X-ray image detecting means comprises converting means for converting into an optical image an X-ray image having passed an object, and a TV camera for converting the optical image into electrical signals; said first rotation mechanism is controlled by said control means to rotate said X-ray source about the horizontal axis together with the collimator in a direction opposite to a direction of inclination of said C-shaped ring member through an angle identical to the angle of the inclination; and said second rotation mechanism is controlled by said control means to rotate said TV camera about the horizontal axis in the direction opposite to the direction of inclination of said C-shaped ring member through an angle identical to the angle of the inclination.

3. The X-ray diagnostic apparatus according to claim 1, wherein said first X-ray source unit comprises an X-ray source for radiating X-rays and a collimator for collimating the X-rays within a predetermined range; said first X-ray image detecting means comprises means for holding a film for fixing an X-ray image having passed an object; said first rotation mechanism is controlled by said control means to rotate said X-ray source about the horizontal axis together with said collimator in a direction opposite to a direction of inclination of said C-shaped ring member through an angle identical to the angle of the inclination; and said second rotation mechanism is controlled by said control means to rotate said first X-ray image detecting means and said film about the horizontal axis in the direction opposite to the direction of inclination of said C-shaped ring member through an angle identical to the angle of the inclination.

4. The X-ray diagnostic apparatus according to claim 1, wherein said first and second rotation mechanisms each have rotating means; and said control means has detection means for detecting the direction and angle of inclination of said C-shaped ring member, and controls each of said rotating means on the basis of the inclination direction and angle detected by said detection means.

5. An X-ray diagnostic apparatus according to claim 1, wherein the control means rotates said first X-ray image detecting means in a direction opposite to a direction of said C-shaped ring rotation at all times and automatically such that focal points of right and left eyes of said first X-ray source are always focused.

* * * * *